United States Patent [19]

Goldberg et al.

[11] Patent Number: 4,696,571
[45] Date of Patent: Sep. 29, 1987

[54] SUSPENDED SEDIMENT SENSOR

[75] Inventors: Marvin C. Goldberg, Englewood; Kirkwood M. Cunningham, Lakewood; Eugene R. Weiner, Denver, all of Colo.

[73] Assignee: The United States of America as represented by the Secretary of the Interior, Washington, D.C.

[21] Appl. No.: 791,286

[22] Filed: Oct. 25, 1985

[51] Int. Cl.[4] ............................................. G01N 15/02
[52] U.S. Cl. ..................................... 356/336; 250/574
[58] Field of Search ............... 356/335, 336, 337, 339, 356/342; 250/564, 574

[56] References Cited

U.S. PATENT DOCUMENTS 4,134,679  1/1979  Wertheimer ......................... 356/336

FOREIGN PATENT DOCUMENTS 1159674  1/1984  Canada ................................. 356/336

Primary Examiner—Eugene R. LaRoche
Assistant Examiner—Robert J. Pascal
Attorney, Agent, or Firm—Thomas Zack; E. Philip Koltos

[57] ABSTRACT

An apparatus is provided for measuring particle sizes between 5 and 50 microns in size and between 10 and 4,000 ppm in concentration prior to dilution of the sample, and upwards to at least 50,000 ppm with dilution of the sample. It is comprised of a laser light source, a square or rectangular sample cell and a photodetector which feeds data to some form of digital processor. The laser light is polarized and the return scattered light is polarized in the same plane. This device functions on the principle that particles in a light beam are capable of scattering the radiation in that beam and that the scattered radiation can be correlated to the physical properties of the scattering particles, specifically size and number.

5 Claims, 17 Drawing Figures

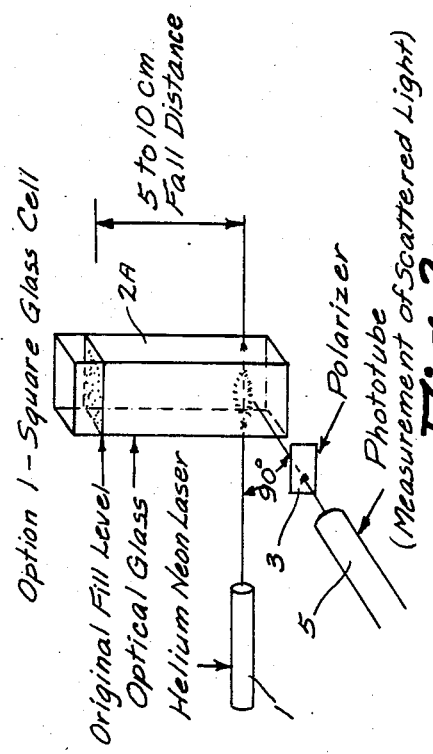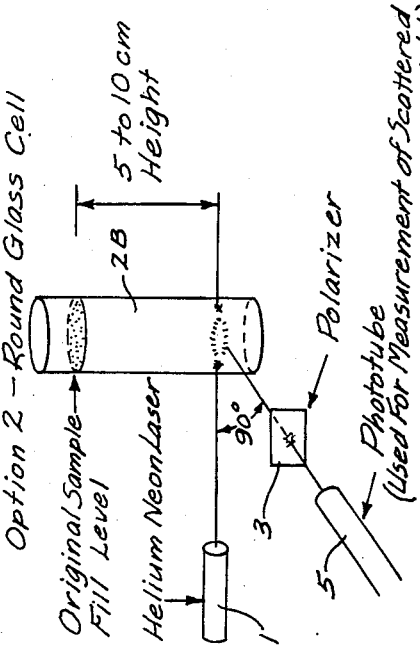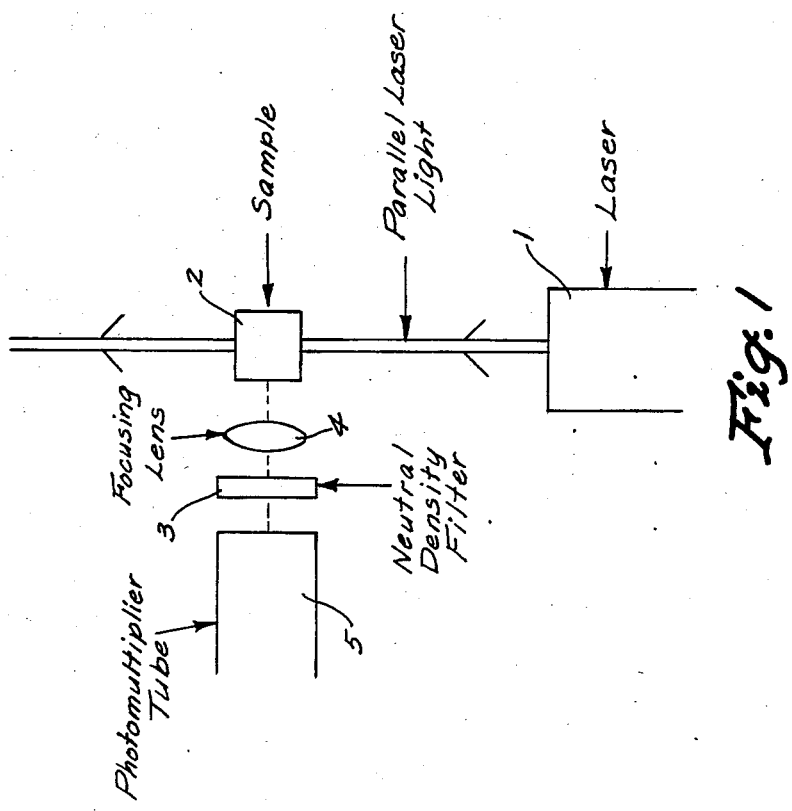

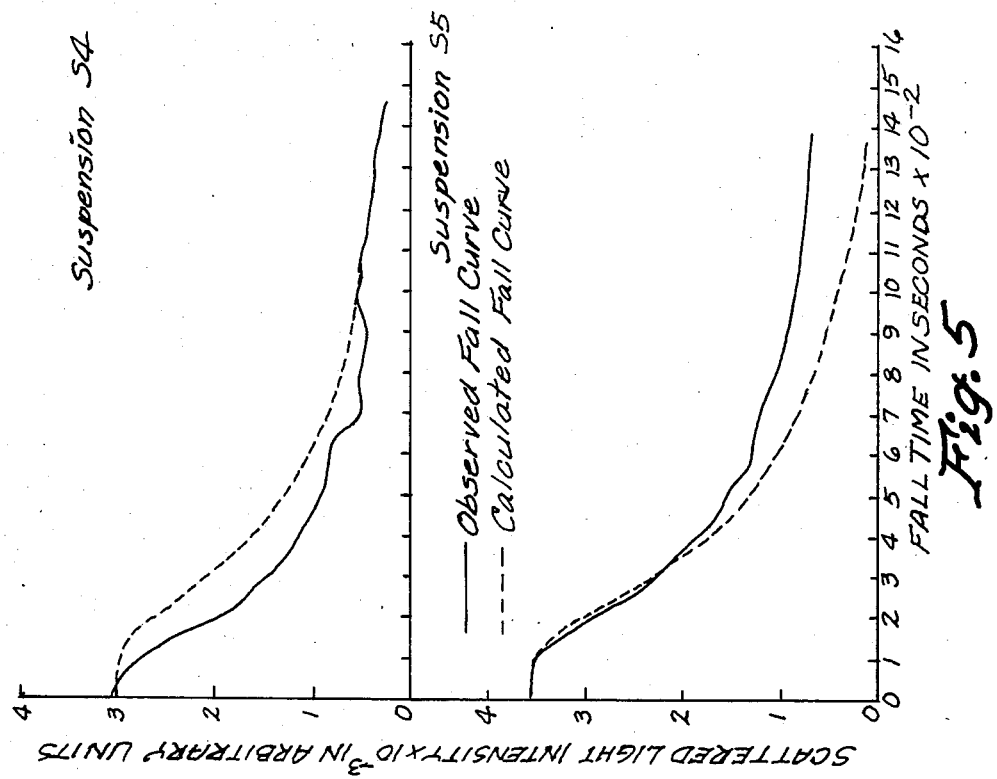
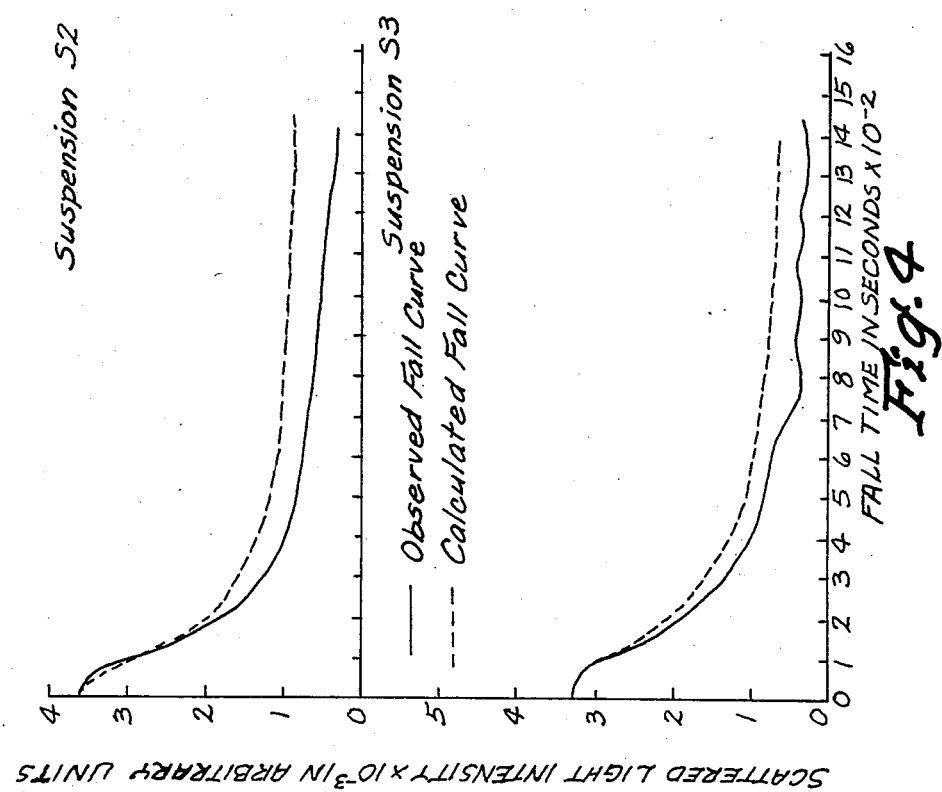

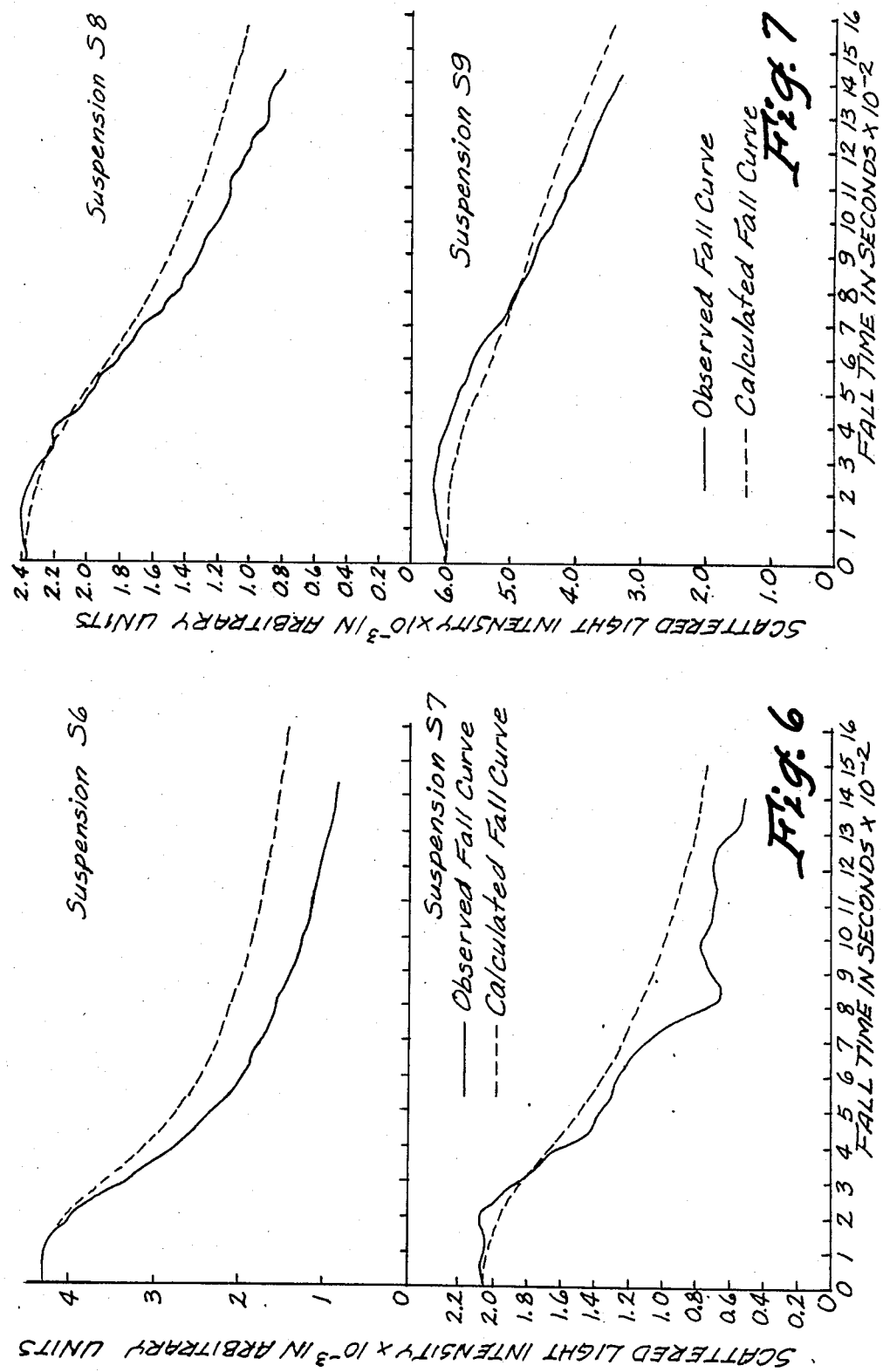

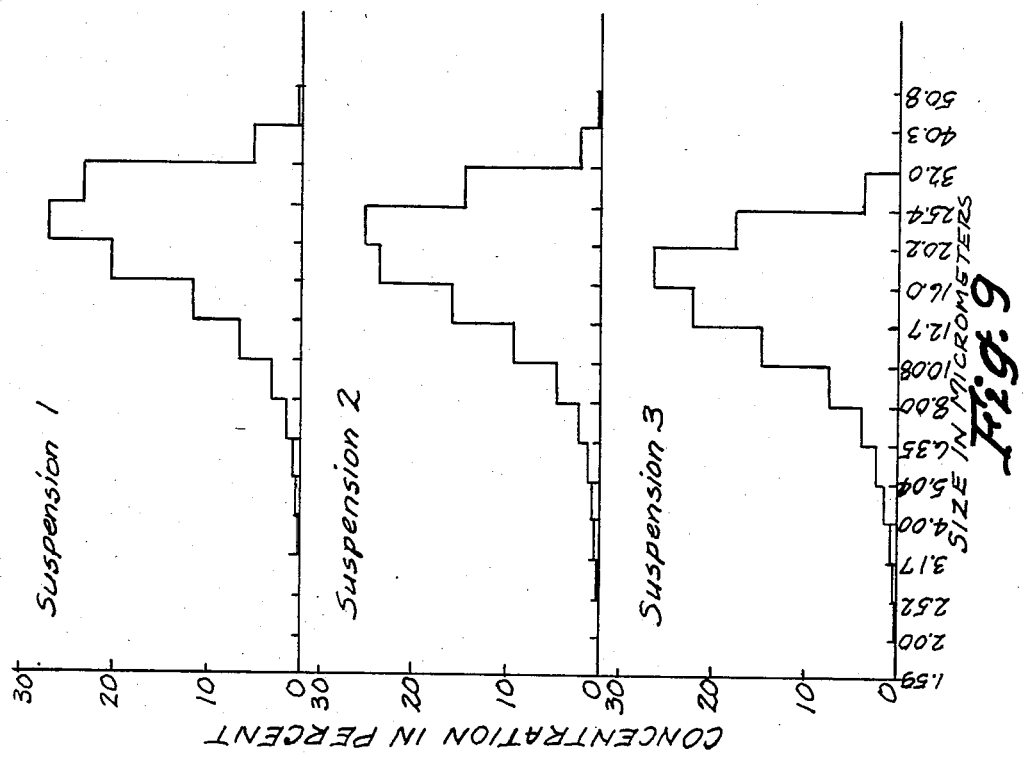
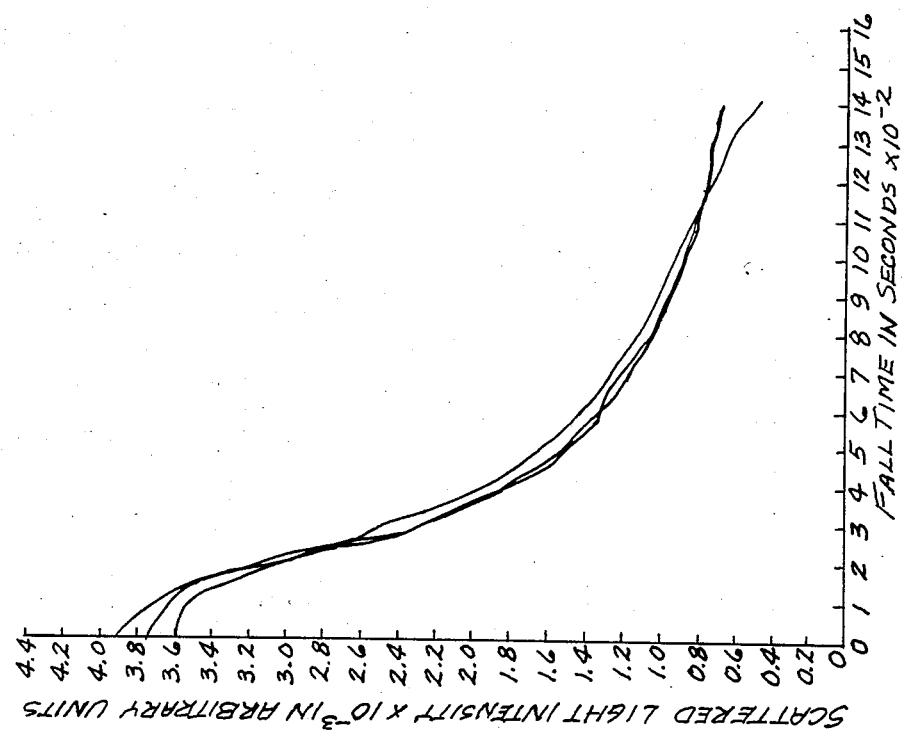

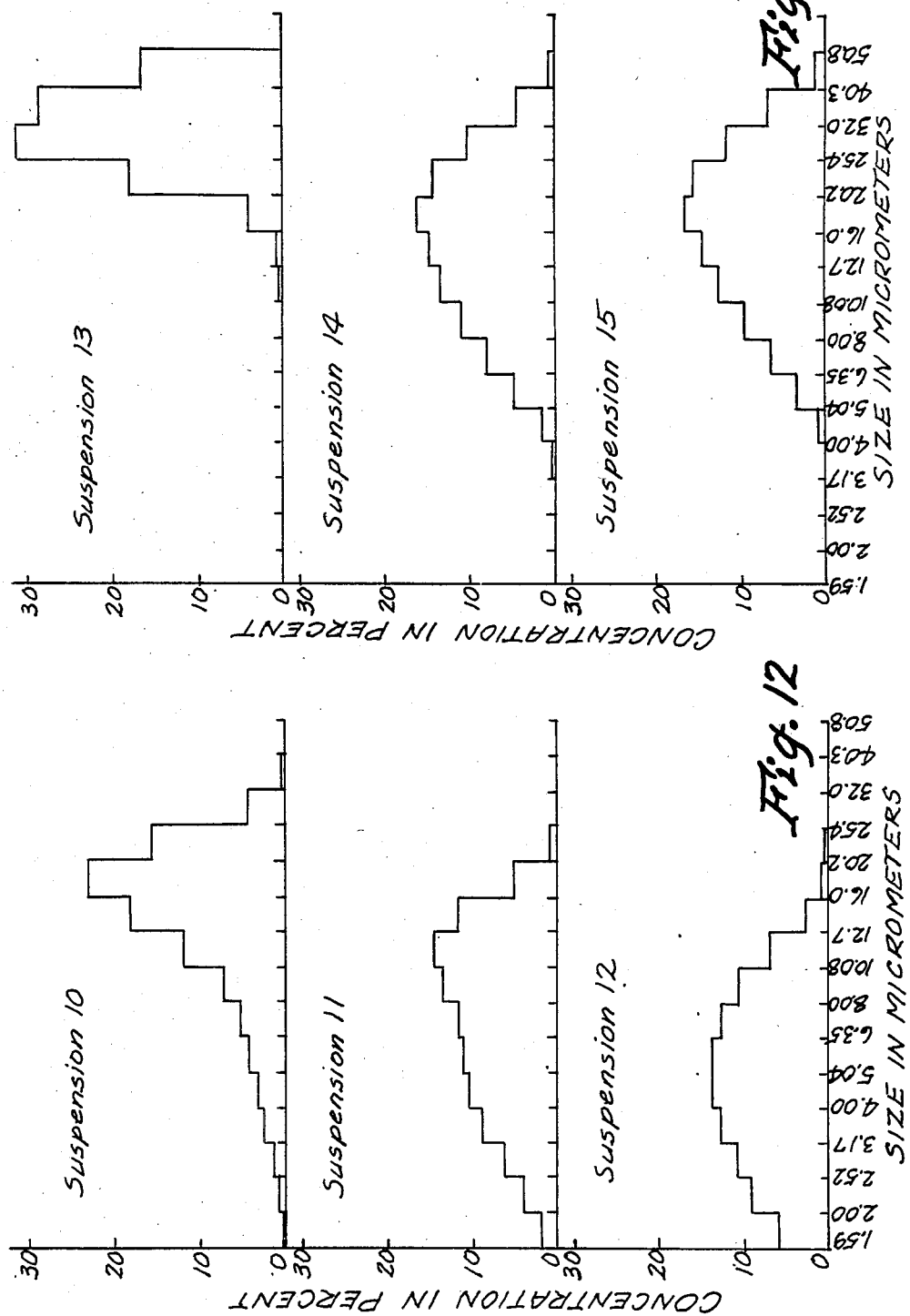

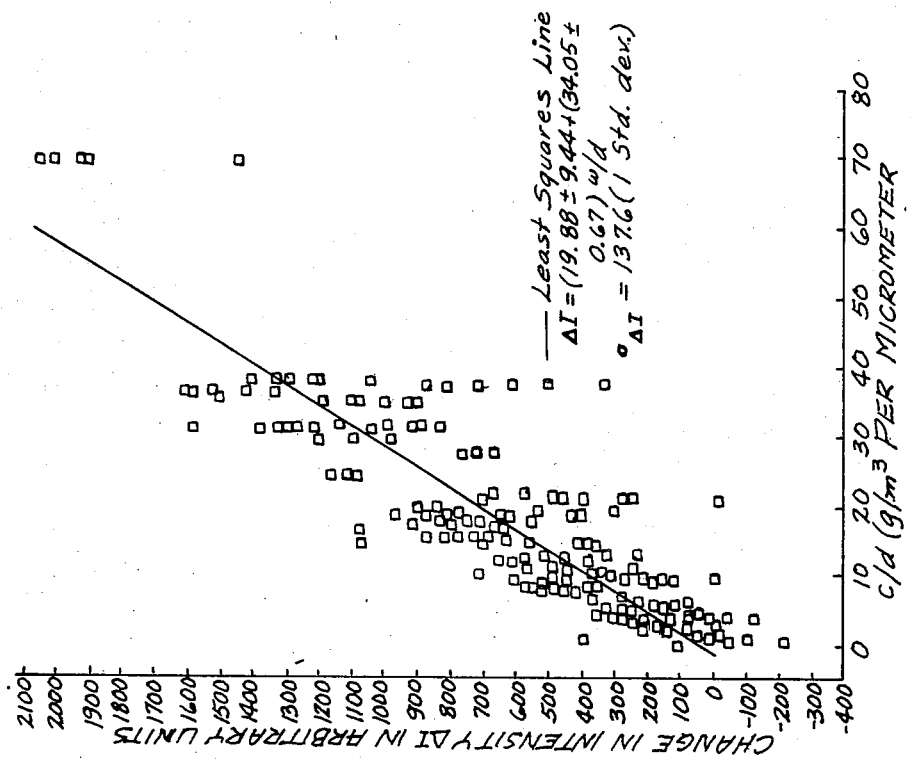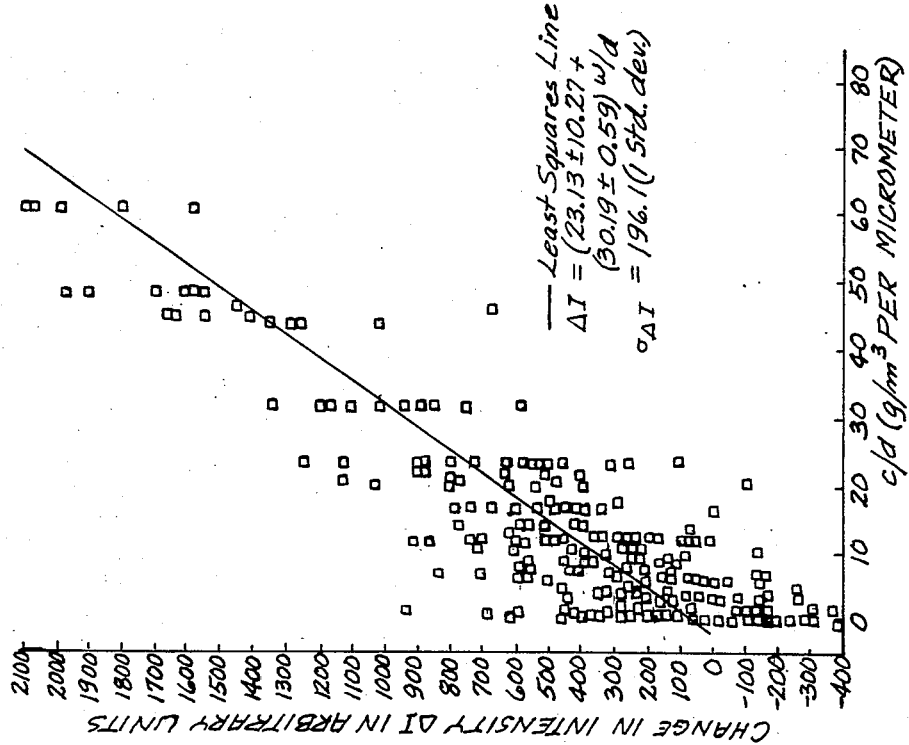

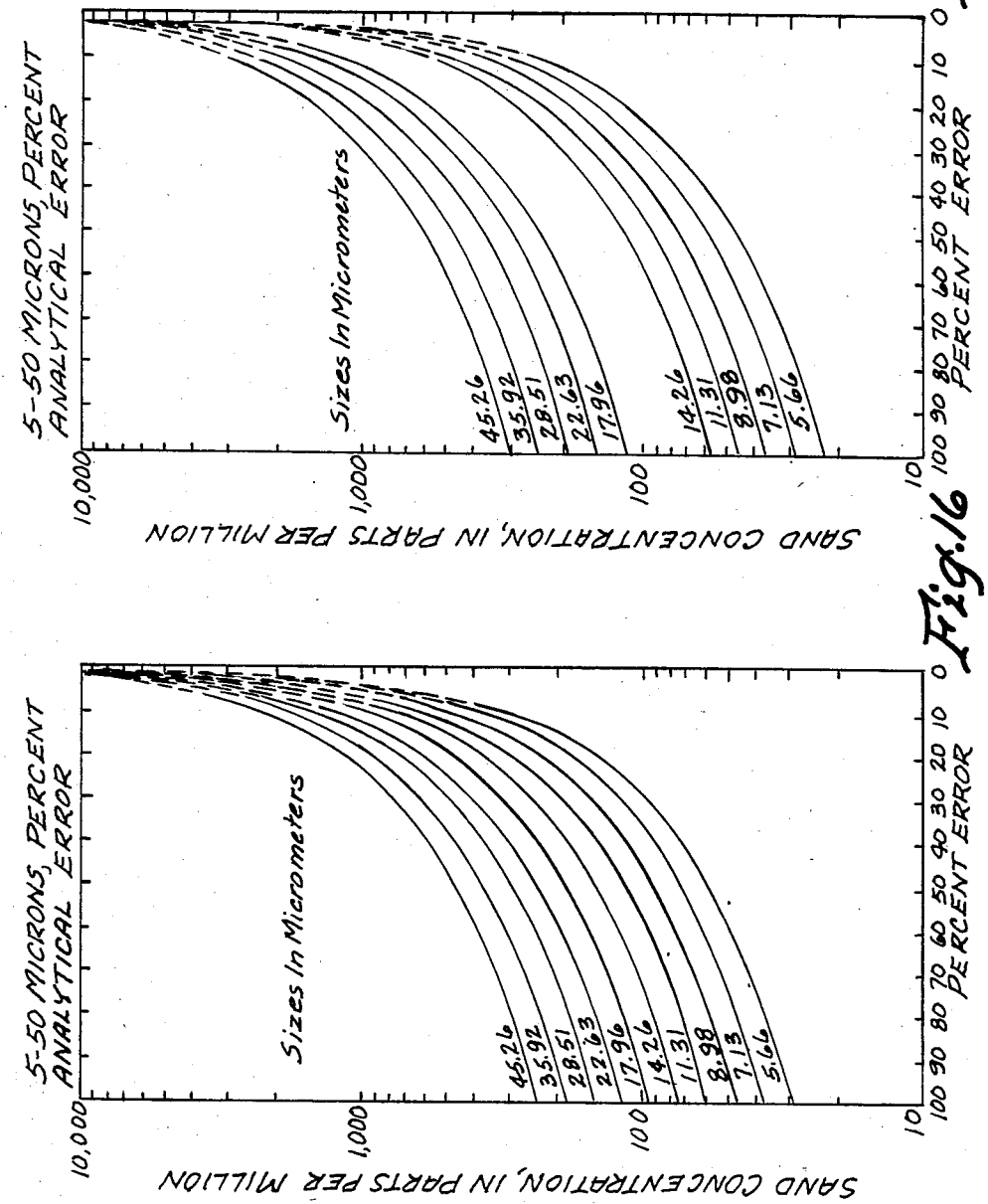

SUSPENDED SEDIMENT SENSOR

TECHNICAL FIELD

The present invention relates to a method and apparatus for measuring the mass and size of suspended sediment in a liquid, and more particularly to such an invention using laser technology.

BACKGROUND ART

Many devices have been proposed which use light scattering alone or sedimentation alone or light scattering or sedimentation in conjunction with other physical methods to define particle size/mass distributions. An article by Terence Allen entitled "Particle Size Measurement", Chapman & Hall, 1974 Chapters 9, 10, 12, 14, discusses these combinations and permutations in detail. However, there appears to be only one reference in the literature to a technique employing light scattering and sedimentation in conjunction, namely an article by Alfred J. Stamm entitled "The Use of Scattered Light in the Determination of the Distribution of Sizes of Particles in Emulsions", J. Amer. Soc., 47:1582-96, (1925).

Devices are known using sedimentation and turbidimetry for particle sizing. They are called photosedimentometers.

There are several A.S.T.M. papers on particle sizing with photosedimentation, for example "A Rapid Method for the Determination of the Specific Surface of Portland Cement"; by L. A. Wagner ASTM Proceedings, vol. 33-II, pp. 553-570 (1933); "Measurements of Particle Size Distributions by Optical Methods" by R. N. Traxler and L. A. H. Baum ASTM Proceedings, vol. 35-II, pp. 475ff (1935); and "Tentative Method of Test for fineness of Portland Cement by Means of the Turbidimeter", ASTM Proceedings vol. 38-I, pp. 746-756 (1938).

The basic methods and principles described in the aforementioned papers and the literature since then relates to specific devices and applications. Turbidimetry measures the portion of the light beam passing through the sample which is not scattered; turbidimetry has a sensitive disadvantage with respect to scattering. The reason is that turbidimetry measures a relatively small decrement in a large signal, whereas scattering represents a substantial increase of light signal on top of a negligible background. The present invention exploits this sensitivity advantage. Otherwise, a scattering-based sedimentation tube has no inherent advantages over a photosedimentometer.

Instruments designed solely for light scattering photometry of fluorescene measurements such as nephelometers or light scattering photometers abound on the market today, but they have not been used in a sedimentation-scattering combination as in the present invention. The aforementioned article by Stamm describes the irradiation of a square cell containing an initially homogenous suspension from two opposite directions with unpolarized white light and the observation of unpolarized scattered light at 90°. The scattered light pattern from the entire length of the cell is recorded on photographic film at various fall times then converted to an analog record with a desitometer. Analysis of the data proceeds in a manner similar to the one described in the invention described below. The chief difference in detail between it and the present invention is that a single frequency, polarized and collimated (laser) beam is used in the present invention as the incident light directed at only one position on the cell, and photoelectric detection of one polarization component of the scattered light. Both of these features contribute to increased detection resolution and sensitivity of the present invention. Because of the limited treatment of data and the different nature of the scattering substance in the Stamm device, it is not possible to make a comparison of sensitivity, detection limits, etc.

U. S. Pat. No. 4,457,624 to Goldberg et al., hereinafter referred to as the patented device, relates to a suspended sediment sensor system for determining the concentration and size distribution of particles in a fluid sample for particle sizes in the range of 50–1,000 microns. There is a need, however, for such a device which measures particle sizes in the range of 5 to 50 microns. Because of this need, the present invention was developed.

The primary differences between this invention and the patented device are the method of obtaining the scattered light from the sample, method of dispersion of the sample, the size range of the sample, the light angle at which the scattered light is detected, size of the cell and the principle of measuring a sample that a loss concentration at the focus of measurement rather than starting at zero and gaining concentration at the focus of measurement.

The detector of the present invention is set at a 90° angle to the incident light, rather than at a back angle of 120° as in the patented device.

The sample is thoroughly mixed in the cell and at time 0 of the measurement, the sample begins to settle out. Interrogation of the change in scattered radiation is made of the completely mixed sample with the full mixture's scttering being measured immediately and the decrease in intensity being measured as a function of time. In the patented device, interrogation of the sample is made only as the settled out particles fall a distance of 30 inches or so through a water column.

In the patented device, the scattered light signal starts at zero and is cycled through a maximum for each size range. In this invention, the signal strength starts at a maximum and diminishes as the measurement proceeds. The sample size range that this invention measures is 5 to 50 microns. The sample size range that the patented device measures is 50 to 1,000 microns. The cell size in this invention is 10 cm. The cell size in the patented device is in the order of 290 cm. The principle of distinguishing the size ranges in the present invention is to allow the smaller particles to scatter light throughout the experiment, whereas in the patented device, the smaller particles only come into the light beam and are scattered light at the end of the measurement and as time progresses, the smaller size particles are measured at the initiation of the measurement time.

DISCLOSURE OF THE INVENTION

This invention is used to measure particle sizes between 5 and 50 microns in size and between 10 and 4,000 ppm in concentration prior to dilution of the sample, and upwards to at least 50,000 ppm with dilution of the sample. It is comprised of a laser light source, a square or rectangular sample cell and a photodetector which feeds data to some form of digital processor. The laser light is polarized and the return scattered light is polarized in the same plane. This device functions on the principle that particles in a light beam are capable of scattering the radiation in that beam and that the scattered radiation can be correlated to the physical properties of the scattering particles, specifically size and number.

This invention is used to examine particles between 5 and 50 microns in size, the particles are homogeneously suspended in a cell and illuminated with polarized laser light and near the bottom of the cell. A detector views the scattered radiation at 90° angle to the light source and in the same plane as the light source. The signal detection continues until all the suspended material has fallen below the plane of the incident light beam. By use of certain mathematical foumulas based on Stokes law of settling, it is possible to calculate, within discrete and small size ranges, the particle size and mass per size range that comprises the sample. Once the mass of each size range is ascertained, the sum of all size ranges in the sample yields the total mass of the sample. The principle set forth herein is compatible to automatic operation and the system could be set up to make measurements unattended, on-site in a river, stream, lake, etc. for up to 14 days performing as many as 36 measurements per day.

In conjunction with a previously reported fall tube particle analyzer that measures particle sizes from 50–1,000 microns and the use of depolarization ratios that measure particle sizes from <1 to 5 microns it should be possible to assemble an instrument to measure particle size —mass rations from <1 to 1,000 microns and from <50 to 50,000 ppm in concentration.

BRIEF DESCRIPTION OF THE DRAWINGS

FIG. 1 is a schematic view of the relative arrangement of apparatus used in a preferred embodiment of the present invention;

FIG. 2 shows a square glass cell holding a liquid sample in the process of being sampled using the present invention;

FIG. 3 shows a round cell glass cell holding a liquid sample in the process of being sampled using the present invention;

FIG. 4 is a comparison of observed and calculated fall time for suspension S2 in the upper graph and suspension S3 in the lower graph; the scattered intensity in arbitrary units versus the fall time in seconds;

FIG. 5 is a comparison of observed and calculated fall time for suspension S4 in the upper graph and suspension S5 in the lower graph; the scattered intensity in arbitrary units versus the fall time in seconds;

FIG. 6 is a comparison of observed and calculated fall time for suspension S6 in the upper graph and suspension S7 in the lower graph; the scattered intensity in arbitrary units versus the fall time in seconds;

FIG. 7 is a comparison of observed and calculated fall time for suspension S8 in the upper graph and suspension S9 in the lower graph; the scattered intensity in arbitraty units versus the fall time in seconds;

FIG. 8 is a precision of data measurements in the square sample cell; three independent measurements of scattered light intensity versus fall time in seconds;

FIG. 9 shows the percent of total mass versus micrometers for three different size distributions; suspension one, the upper figure size distribution, ranges from 3.17 to 50.8 micrometers; suspension 2, the middle figure size distribution, ranges from 2.52 to 50.8 micrometers suspension 3, the lower figure size distribution, ranges from 2.0 to 32 micrometers;

FIG. 12 shows the percent of total mass versus micrometers for three different size distributions; suspension ten, the upper figure size distribution, ranges from 1.59 to 40.3 micrometers; suspension eleven, the middle figure size distribution, ranges from 1.59 to 25.4 micrometers; suspension twelve, the lower figure size distribution, ranges from 1.59 to 32.0 micrometers;

FIG. 13 shows the percent of total mass versus micrometers for three different size distribution; suspension thirteen, the upper figure size distribution, ranges from 10.8 to 50.8 micrometers; suspension fourteen, the middle figure size distribution, ranges from 3.17 to 50.8 micrometers; suspension fifteen the lower figure size distribution, ranges from 4.00 to 50.8 micrometers;

FIGS. 14 and 15 show the change in intensity in arbitrary units as plotted against calibration data; and FIGS. 16 and 17 show plotting of calibration data values from a Coulter Counter and ΔI values from the smoothed fall curves for the square and round sample cells respectively.

BEST MODES FOR CARRYING OUT THE INVENTION

Figure 11:
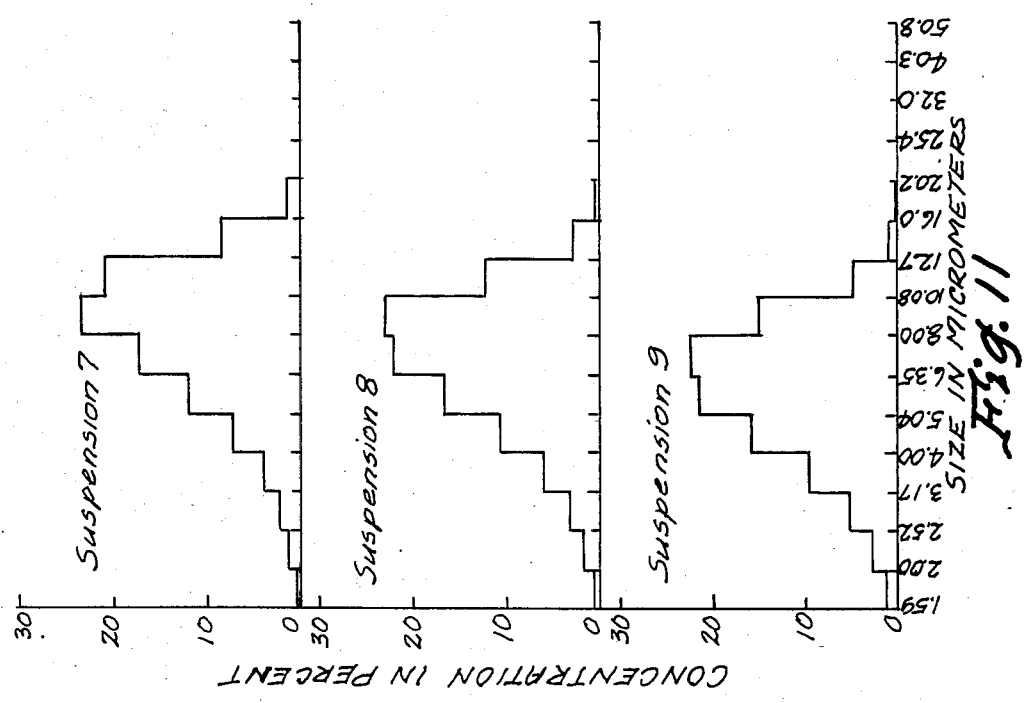
FIG. 11 shows the percent of total mass versus micrometers for three different size distributions; suspension seven, the upper figure size distribution, ranges from 1.59 to 25.4 micrometers; suspension eight, the middle figure size distribution, ranges from 1.59 to 20.2 micrometers; suspension nine, the lower figure size distribution, ranges from 1.59 to 20.2 micrometers.

The sample cells used to measure particles in the 50 to 50 μm range are pictured in FIGS. 1 and 2. As shown in FIG. 1, parallel polarized laser light from the laser (1) is used to illuminate the sample (2). The sample is held in a cell, (square or round) (see FIG. 2) 1 cm ×1 cm on a side and between 5 to 10 cm long. Calibration must be performed on the same cell as is used to run the sample. The light that scatters from the suspended particulates is detected at right angles to the sample containing cell. Inserted in the optical path of the detector is a neutral density filter (3), a focusing lens (4) to focus the scattered light into the detector and a photomultiplier tube (5) to detect the light. The signal goes through an amplifier to a computer. The scattered light was detected in both cases with an RCA No. 8645 photomultiplier tube operated at 900V—although other similar equipment could be used and the signal amplification employed a Keithley 1427 current amplifier, again other similar equipment could be used. Neutral density filters were employed as needed to keep the amplified scattering signal in the range −5 to +5 volts. This letter is a characteristic that satisfies our analog to digital converter which processes the signal prior to processing and storage in the computer and is not a necessary embodiment of the invention.

Operation

Sediment containing suspensions are added to the sample cells, and the cell plus the contents are shake vigorously. At the end of the shaking time, the Schmitt trigger or other such computer attached signal device activates data taking. The first few seconds of data points are a "dark background" and cannot be used for particle sizing. Measurements of scattered intensity are taken continuously as the sample settles to the bottom of the sample cell. This is continued until the smallest size of interest, usually 5.0 μm, falls below the scattering plane. Either exactly the same column height of suspension is measured each time or the distance from the sample's surface to the position of the laser beam is measured for each sample. This distance enters the fall calculations as the fall distance s in equation (3). Intensity values are recorded continuously as the settling takes place.

Theory

Before discussing the calibration measurements themselves, it is necessary to review some aspects of the physical model used to interpret the data. Stoke's law is the most important element of this model because it allows one to relate fall velocity to particle sizes and densities, i.e.

$$\frac{ds}{dt} = \frac{(\rho s - \rho f)}{18\eta} gd^2, \text{ or since} \tag{1}$$

or since none of the right hand parameters are functions of time, $$s = \frac{(\rho_s - \rho_f) gd^2 t}{18\eta} \tag{2}$$

where t=settling time for settling distances s, $\rho_s \rho_f$=densities of solid particles and liquid medium respectively, g=gravitational constant, $\eta$=fluid viscosity, and d=equivalent sphere particle diameter. If g is in m/s, $\rho$ in kg/m$^3$, t in seconds, s in cm., $\eta$ in kg/m$-$s (at 20° C., the temperature at which experiments were carried out), and d in micrometers, then $$s = 8.99 \times 10 d^{-5} t^2 \tag{3}$$

Thus, using equation (3) and known s, one can calculate the settling time for a desired size d.

The second important element of the model is a general expression which relates the amount of vertically or horizontally polarized backscattered light to the mass concentration, c, of particles of a given size, d, that is I=(c,d). A good zeroth-order approximation might be that the amount of scattered light is proportional to the total particle geometric cross section encountered by the laser beam, $$I(\text{total}) = \Sigma I_i \alpha \Sigma N_i \sigma_i \tag{4}$$

Where $N_i$=number density of particles in size range i
  $\sigma_i$=geometric cross section of particles of mean size $d_i$ in range i
  $I_i$=backscattered intensity (parallel or perpendicular) from size range i In this context, $d_i$ is the mean sphere equivalent size in range i. If we further assume that $$N_i \alpha C_i / d_i^3$$

with $C_i$ in ppm, and $\sigma_i \alpha d_i^2$, then $$I_i \alpha C_i / d_i \tag{5}$$

In the calibration procedure, $C_i$ and $d_i$ are known from Coulter Counter measurements and $I_i$, actually $\Delta I_i$, is the quantity measured from fall curves. Comparison of the two sides of (5) should test the basic corrections of the relation and the supply proportionally factor(s).

Data Processing

Step 1 is to examine the shape of the fall curves. In the fall cell calibration procedure, fall distance varies from one run to the next, so curves cannot be directly added together to reduce noise. Therefore, only one representative curve measured on a particular suspension is shown in FIGS. 4-8 for a square cell data for suspension S2-S9. Each graph also contains a calculated fall curve. The size/mass distribution and fall distance for the particular run was used, the proportionality factor between $\Delta I$ and c/d was taken from the square cell calibration plot (see discussion to follow), and the initial intensity was taken from the empirical curve to account for any spurious background intensity. Comparison of observed and calculated curves allows comparison between actual and theoretically expected behavior. FIG. 8 shows three curves for the same suspension S5, run at the same initial concentration to give an idea of the reproductability of data for the square fall cell.

Figure 10:
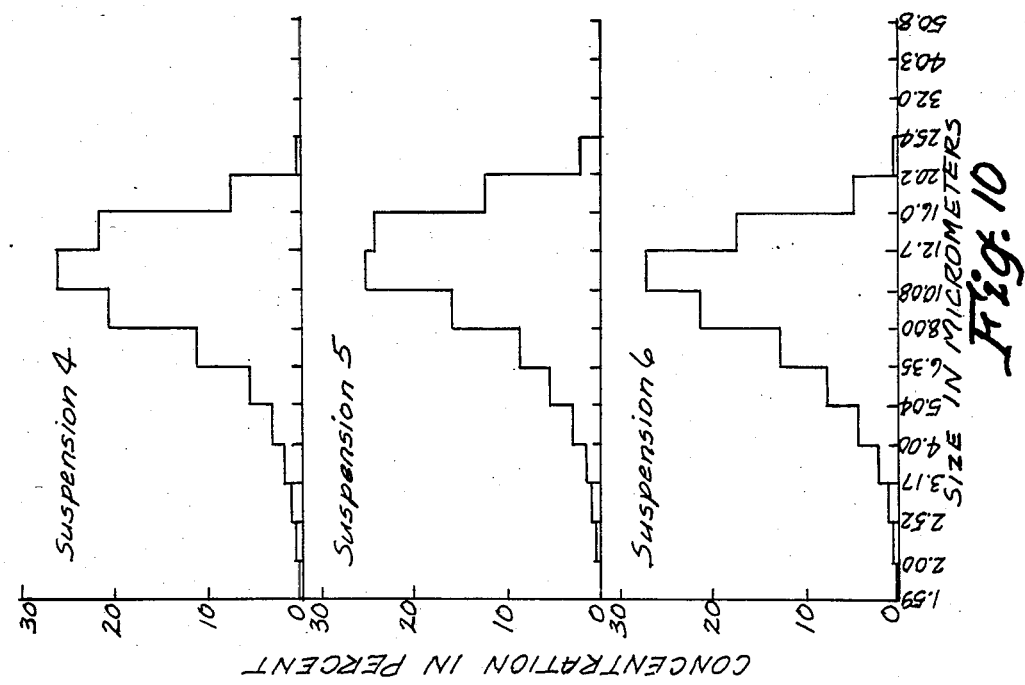
FIG. 10 shows the percent of total mass versus micrometers for three different size distributions; suspension four, the upper figure size distribution, ranges from 1.59 to 25.4 micrometers; suspension five, the middle figure size distribution, ranges from 1.59 to 25.4 micrometers; suspension six, the lower figure size distribution, ranges form 1.59 to 25.4 micrometers.

It is obvious from FIGS. 4-8 that the small volume of the fall cell, whether round or rectangular, results in a much closer appromoximation to the physical assumption of Stoke's law. Another test of this is the calibration plots for the round and square cells. The model postulated for the scattering processes should result in a linear relation between $\Delta I$ and c/d that goes through the Q,O origin and has minimal scatter. The suspensions shown graphically on FIGS. 9-13 were used to calibrate to system. c/d values from the Coulter Counter and $\Delta I$ values from the smoothed fall curves were obtained as before, and are plotted in FIGS. 16 and 17 for the square and round sample cells respectively. There are two calibration curves for the square cell data because the initial analysis showed that disaggregation of the data into 16-45 micron and 5.0-16 micron portions yielded two calibration curves with smaller errors in the curve fitting parameters than would be the case for one calibration curve representing all the data. Nothing is gained by disaggregating the round cell calibration data. $\sigma \Delta I$ in FIGS. 14 and 15 is the standard deviation in the $\Delta I$ direction of all the points about the least squares line. The nature of the data in FIGS. 14 and 15 indicate that the physical model assumed is fairly good. Despite a fair amount of scatter, the data obviously have a linear trend intersecting the origin.

The calibration data may be used to estimate the error in the concentration value for a given size element generated by any arbitrary measurement. Starting with the basic calibration $$\Delta I = A + B(c/d) \tag{6}$$

assume, first, that the equation applies to a given sample; second, that the error in d is negligible compared to other errors; and third, that the distribution of $\Delta I$ values about the least squares line is gaussian, with $\sigma_{\Delta I}$ independent of c/d. The second assumption is probably always valid for the fall cells. as long as temperature is known, or controlled, and no agent is present in the suspension that affects solvent viscosity, i.e., a large amount of surface-active agent. The third assumption appears to be reasonable 1st approximation on the basis of the visual appearance of the date in FIGS. 16 and 17.

Precision of Measurement

Granting assumptions, a conventional propagation of errors treatment yields:

$$\sigma_c = \frac{d}{B} \sqrt{\frac{\sigma^2}{\Delta I} + \sigma_A^2 + \frac{c^2 \sigma_B^2}{B^2}} \quad (7)$$

where d is in microns, c in ppm.

The standard deviation of A, B and $\Delta I$ may be found in FIGS. 13 and 14. These numbers all represent one standard deviation, e.g., the values of the numbers have a likelihood of 70% of being within the error limits. Substituting these values yields the following:

Sizes 16–50 $\mu$m, square fall cell $$\sigma_c = d\sqrt{42.31 + 4.190 \times 10^{-7} c^2} \quad (8)$$

Sizes 5–16 $\mu$m, square fall cell $$\sigma_c = d\sqrt{16.41 + 3.340 \times 10^{-7} c^2} \quad (9)$$

Sizes 5–50 round fall cell $$\sigma_c = d\sqrt{26.77 + 2.268 \times 10^{-7} c^2} \quad (10)$$

Defining the percentage error as 100 $\sigma_c$/c allows one to graph ppm versus percent error as a function of size. FIGS. 16 and 17 contain these graphs for equations (8), (9) and (10), respectively.

Resolution

In addition to error, it is also necessary to have some idea of the resolution of the fall cells. There are two sources of information on this question. First, poor resolution affects $\Delta I$ versus c/d plots by causing a non-zero intercept at c/d=0. The reason for this is that any broadening of the measured distribution compared to the actual distribution produces $\Delta I$ values at the wings of a distribution which are consistently high. There is no evidence for systematicaly high $\Delta I$ values in FIGS. 14 and 15, at leats within experimental scatter. Second, direct comparison can be made between actual and measured distributions for suspension which have a fairly narrow distribution.

Summary of Properties of the Fall Cells

Resolution is as shown in Table 1, analyzable range of particle sizes 5–50 $\mu$m in experiments reported here. Smaller sizes than 5 $\mu$m can be analyzed if more time than 45 minutes is allowed. Analysis of sizes larger than 50 $\mu$m can be done in principle but would suffer from a large error factor. Sensitivity is defined in general by equations (8–10). Analyzable concentration range without introduction of significant systematic errors; 10 ppm to about 4,000 ppm. Lower concentrations must be run multiple times to get acceptable percent error levels. At the upper limit, the calibration curve becomes non-linear and Stoke's law begins to fail because particles of all sizes tend to fall together at the same rate. The upper range of any sample measurement is unlimited if dilutions are made to restore the measurable range as stated above.

TABLE 1

| Size Range (Microns) | 5–50 Size Ranges Mean Size (Microns) | Resolution |
|---|---|---|
| 5.04–6.35 | 5.66 | ±.5 |
| 6.35–8.00 | 7.13 | ±.8 |
| 8.00–10.08 | 8.98 | ±1.0 |
| 10.08–12.7 | 11.3 | ±1.0 |
| 12.7–16.0 | 14.3 | ±1.7 |
| 16.0–20.2 | 18.0 | ±1.9 |
| 20.5–25.4 | 22.6 | ±2.0 |
| 25.4–32.0 | 28.5 | ±3.3 |
| 32.0–40.3 | 35.9 | ±4.1 |
| 40.3–50.8 | 45.3 | ±5.3 |

Obviously, many modifications and variations of the present invention are possible in light of the above teachings. It is therefore to be understood that, within the scope of the appended claims, the invention may be practised otherwise than as specifically described.

We claim:

1. An apparatus for simultaneously measuring particle mass and size of suspended sediment in liquids comprising:
   means for holding a sample of liquid having sediment of a size between 5 and 50 microns suspended therein to be measured, said sediment size being large enough to cause immediate settling of said sediment under the mere influence of gravity, undisturbed by convection flows or external forces, said holding means containing said sample of liquid;
   light surce means for producing laser light beam polarized in a predetermined plane and directing said laser light beam through said sample holding means during at least a portion of the time that said sediment is settling;
   photodetector means disposed at an approximately 90° angle with respect to said laser light beam for detecting the amount of light from said light source means passing through said sample holding means at said 90° angle; and
   means disposed between said sample holding means and said photodetector means for polarizing the light being detected by said photodetector means in the same plane as the polarization of said laser light beam.

2. The aparatus of claim 1 including:
   a digital processor; and
   means for feeding the output of said photodetector means to said digital processor.

3. The apparatus of claim 1 including:
   data recording means for collecting and storing data relating to the time variation of the amount of light detected by said photodetector means.

4. A method of simultaneously measuring particle mass and size of suspended sediment in liquids comprising:
   obtaining a sample of liquid having sediment of a size between 5 and 50 microns suspended therein, said sediment size being large enough to cause immediate settling of said sediment under the mere influence of gravity, undisturbed by convection flows or external forces;
   directing a laser light beam, polarized in a predetermined plane, through said sample during at least a portion of the time that said sediment is settling;

detecting the amount of light passing through the sample from said laser light beam by use of a photodetector disposed at approximately 90° with respect to the direction of said laser light beam; and polarizing the light being detected by the photodetector in the same plane as the polarization of said laser light beam.

5. The method of claim 4 including a step of recording the time variation of the amount of light detected by the photodetector.

* * * * *